(12) United States Patent
Ibay

(10) Patent No.: US 8,655,633 B2
(45) Date of Patent: Feb. 18, 2014

(54) METHOD OF PREDICTING THE PHYSICAL PROPERTIES OF POLYURETHANE MATERIALS

(75) Inventor: Augusto C Ibay, Acworth, GA (US)

(73) Assignee: Augusto C. Ibay, Acworth, GA (US)

( * ) Notice: Subject to any disclaimer, the term of this patent is extended or adjusted under 35 U.S.C. 154(b) by 256 days.

(21) Appl. No.: 13/066,628

(22) Filed: Apr. 19, 2011

(65) Prior Publication Data

US 2012/0271600 A1 Oct. 25, 2012

(51) Int. Cl.
  *G06F 7/60* (2006.01)
  *G06G 7/48* (2006.01)
  *C08J 9/00* (2006.01)

(52) U.S. Cl.
  USPC .................................. 703/12; 703/2; 521/49

(58) Field of Classification Search
  None
  See application file for complete search history.

(56) References Cited

U.S. PATENT DOCUMENTS

| | | | |
|---|---|---|---|
| 5,260,882 A * | 11/1993 | Blanco et al. | 703/6 |
| 5,624,971 A * | 4/1997 | Wilson | 521/137 |
| 6,687,621 B2 * | 2/2004 | Schneiderman et al. | 702/27 |
| 2009/0292035 A1 * | 11/2009 | Semmes | 521/141 |

* cited by examiner

*Primary Examiner* — Omar Fernandez Rivas
*Assistant Examiner* — Nithya J Moll
(74) *Attorney, Agent, or Firm* — Paul Dalley

(57) ABSTRACT

The specification relates to the formulation of polyurethane materials particularly polyurethane and polyisocyanurate foams. The specified method allows the formulator to mathematically predict the final physical properties of the polyurethane and polyisocyanurate foams by using the algorithm described herein.

9 Claims, 2 Drawing Sheets

METHOD OF PREDICTING THE PHYSICAL PROPERTIES OF POLYURETHANE MATERIALS

BACKGROUND OF THE INVENTION

This invention pertains to the formulation of rigid polyurethane and polyisocyanurate foam, and more particularly to a method that allows the formulator to predict physical properties of a formula prior to experimental determination. Rigid foam can be defined as a stable dispersion of gas in a solid rigid phase, said rigid phase being a polyurethane or polyisocyanurate polymer. It is common in art to refer to both polyurethane and polyisocyanurate foams as polyurethane foam. This convention will be maintained herein.

Polyurethane foams are products of significant commercial importance, being used in such useful commercial products ranging from building insulation, sound dampening materials, to gaskets, bedding and seat cushions. All of the products mentioned are a formulated material; that is they are created by the careful selection and blending of a plurality of individual components that are then mixed together using a specific manufacturing process to produce the final product. It is the task of the formulator to select the individual raw materials and proportion them with respect to each other into a final formula or recipe that with proper processing will produce the desired product. Formulation is often a repetitive process whereby the formulator prepares a written formula, then mixes it in the laboratory, tests a specimen made from the formula to determine its physical properties. The tests results are then compared to the design criteria. If the design criteria are not met, then the process is then repeated until the design criteria are met.

Formulation is a time consuming, expensive, and waste generating process. It consumes labor hours to design and test the formulas, raw materials to produce the test specimens, and the failed formulations generate waste that must be land filled. Thus a method that reduces the number of trial formulations to be produced and tested is a useful and desirable method. The invention described herein enables the formulator to reach the design criteria with less effort than the current art.

If the formulator could accurately predict the final physical properties of the written formula without having to complete an experimental trial for each formula, the number of experimental runs could be reduced. One of the preferred methods to reduce the number of experimental runs is to use statistical methods, often referred to as design of experiments or DOE. By entering a range of proportions of a series of raw materials, DOE is used to create a response surface map. The map describes a design space consisting of actual and theoretical physical properties of different formulas. Once the response surface map is created, theoretical formulas can be selected from the response surface map. The formulator then scans the response surface to find a theoretical formula the meets the design criteria. The formulator then prepares and tests the formula to confirm the predicted results.

Although DOE is effective, it is limited when compared to the method described herein. To use DOE the formulator must run multiple of experiments to create and map the design space. The method described herein, does not require the formulator to create a mapped design space. Rather it predicts final physical properties of each formula without requiring the formulator to prepare and test the formulation. In this way the invention is advantageous over the current art because the formulator does not have to prepare multiple formulas, instead he prepares only the formulas that match or closely approximate the design criteria.

SUMMARY OF THE INVENTION

According to the present invention, the foregoing advantages are obtained by creating a database or list of the numerical physical properties of at least two raw materials. The formulator then selects the raw materials from the database; and creates a formula by proportioning the raw materials with respect to each other, the formula being a list of the numerical proportions of each of the raw materials. The physical properties of the formulation are then calculated by hand with the aid of a slide rule and mathematical tables using a defined algorithm. The algorithm being a series of defined mathematical equations carried out in a specific sequence that will estimate the physical properties of the formula.

If the calculated properties do not meet the design criteria, then the formulator either, adjusts the ratio of the previously selected raw materials with respect to each other, or adds an additional raw material or materials, or removes a raw material, or removes and replaces it with another, or with several additional raw materials. Each time a new formulation is created, the algorithm is used to calculate the physical properties of the formula. The process is repeated until the design criteria are met. The formulator then confirms the predicted results by preparing and testing the formula experimentally.

In accordance with another aspect of the invention, the raw material database, the proportional values of the formula and the equations that comprise the algorithm are managed by a computer and software. The computer could be any microprocessor enabled device with a basic input and output system, for example, without limitation, a personal computer, mainframe computer, calculator, or program logic controller also called a PLC. The software could be a spread sheet program that allows for the creation of a database, entering the numerical proportions of the formula, the numerical physical properties of the raw materials, and the equations that comprise the algorithm. The spread sheet should be capable of manipulating the entered data so that the appropriate numerical values are entered into the equations that comprise the algorithm and performing the calculations. The software could also be code written to allow for the creation of a list of numerical physical properties of the raw materials, and allow for entering the values for the formulation, and then running the calculations that comprise the algorithm.

In yet another aspect of the invention, a calculator or a PLC could be used to practice the invention. Although handheld calculators are less powerful than computers, they are capable of storing the required data and running the calculations required by the algorithm. Similarly a PLC's, which are used to control and run manufacturing equipment, could be designed to create a database of the numerical physical properties of the materials being processed by the machine, allow for the entering of a formula using the raw materials listed in the database, and then running the algorithm and displaying the results. In this way the formulator could implement the new formula on the fly without having to return to the laboratory.

The final physical properties of rigid polyurethane foams can be predicted through the use of both chemical and engineering mathematical equations. Equations 1-7 below are the mathematical equations necessary to practice the invention. The equations listed in order provided for below comprise the algorithm that will predict the final physical properties of the foam which are the density, as well as the compressive, tensile, and flexural strength of the product Equations 5, 6, and 7 respectively.

DESCRIPTION OF THE PREFERRED EMBODIMENT

Figure 1:
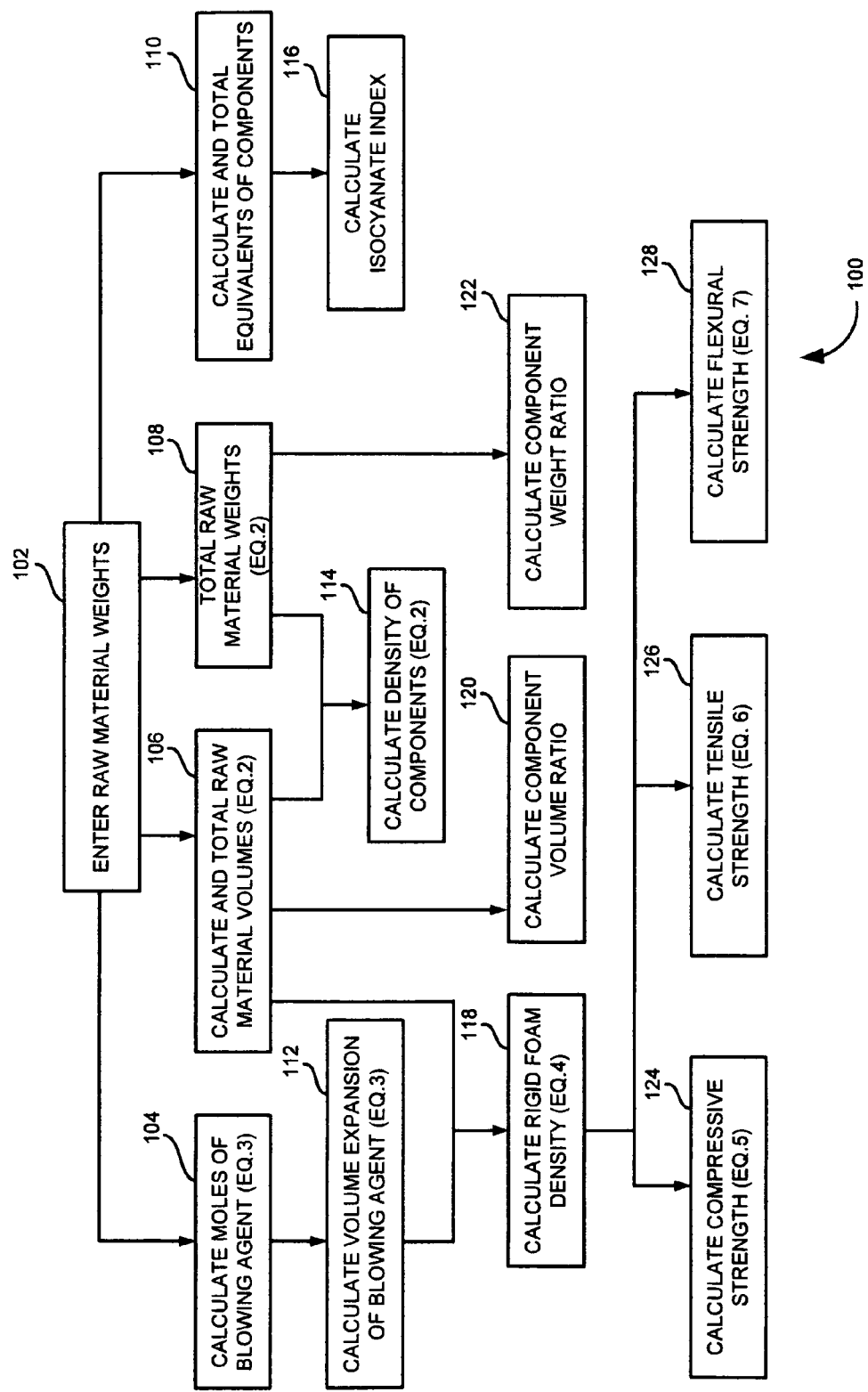
FIG. 1 is a block diagram of the algorithm.
Figure 2:
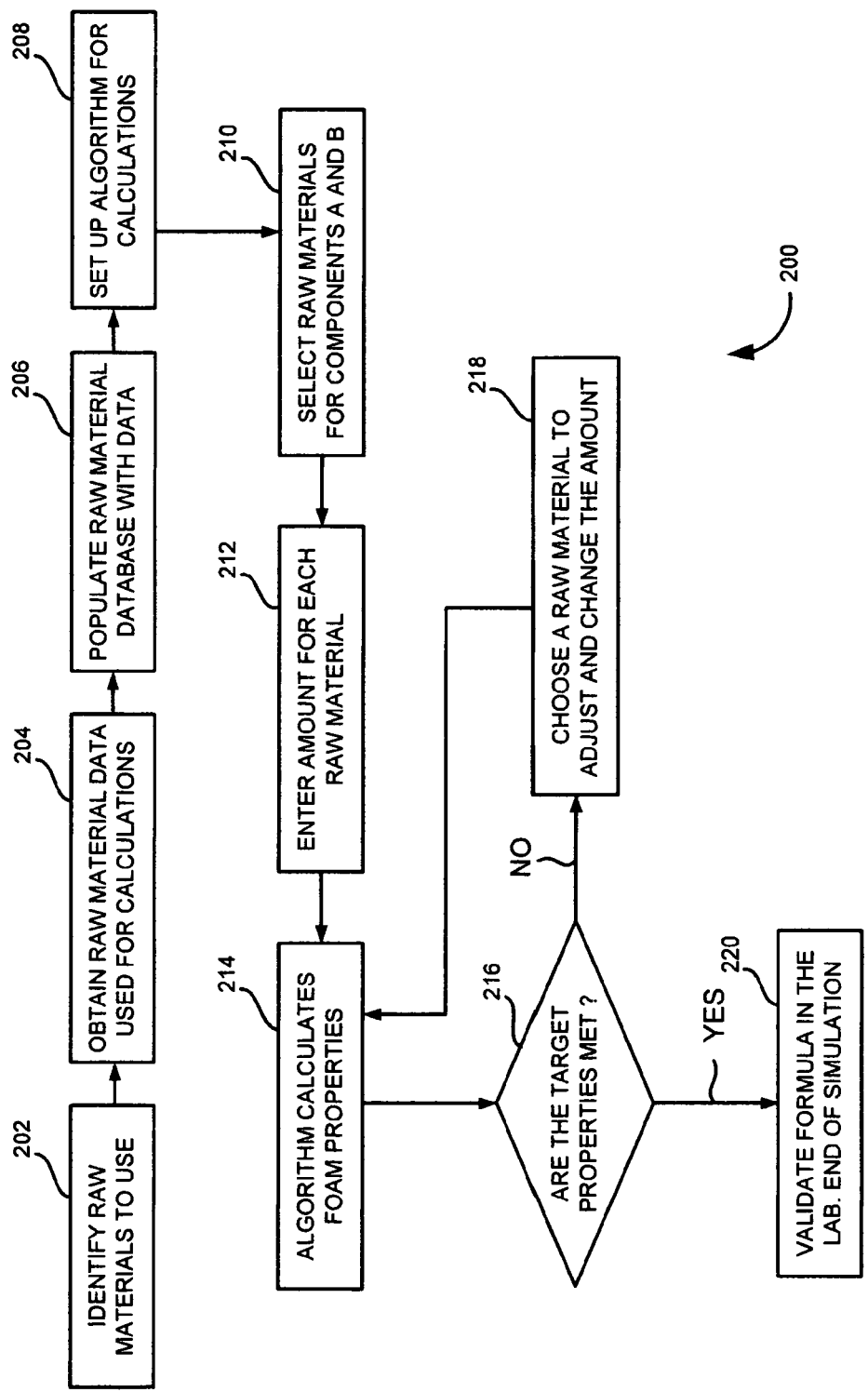
FIG. 2 is block diagram listing the steps recommended to practice the invention.

The following provides a description of the preferred embodiment of the invention, but in no way limits the invention. Other configurations are possible. To practice the method, the formulator first populates the material database 206 with at least the specific gravity of each raw material and molecular weight of the blowing agents 204. Other information 204 such raw material name, viscosity, functionality, equivalent weight, and milliequivalents per gram could be added as well. Second, the formulator determines the target physical properties for the polyurethane foam.

Third, the formulator selects at least two raw materials, and a blowing agent from the database 206. Any formula must contain at least one polyol, one isocyanate and one blowing agent 210. Fourth, the formulator formulates the product. Formulating consists of two steps, (a) proportioning the ratio of the raw materials and the blowing agent with respect to the other which yields a formula or recipe for a mixture 210; and (b) applying a series of algorithms 214 using the numerical physical properties of the polyol, isocyanate, and blowing agent 204, and the numerical proportions of the formula to estimate the physical properties of the product 212. Steps (a) and (b) are repeated until the estimated physical properties match or are an acceptable approximation of the target physical properties 216. Lastly, the formulator confirms estimated properties experimentally by preparing and testing the resulting formula 220.

The physical properties of the formula are predicted by using the numerical raw material 204, proportional data 212, and the algorithm described by Equations 1-7 below.

$$\text{Volume} = \text{mass} \div \text{density} \quad \text{Eq. 1}$$

$$\text{Density Calculation:} \quad D = \frac{M_1 + M_2 + M_3 + \ldots M_n}{V_1 + V_2 + V_3 + \ldots V_n} \quad \text{Eq. 2}$$

Where:
D=density of mixture in grams per milliliter
M=mass of each component in grams
V=volume of each component as calculated from specific gravity or density $$\text{Gas expansion calculation:} \quad PV = nRT \text{ or } V = \frac{nRT}{P} \quad \text{Eq. 3}$$

Where:
P=pressure in Pascals
V=volume in cubic meters (converted to milliliters after calculation)

n=moles of substance (calculated from molecular weight of blowing agent)
n=mass/molecular weight
R=8.314472 J·K−1·mol−1 (Regnault gas constant)
T=temperature in Kelvin (predicted exotherm of chemical reaction)

$$\text{Foam Density Calculation: Foam Density} = m_t/(V_t + V_g) \quad \text{Eq. 4}$$

Where:
$m_t$=total mass of mixture in grams
$V_t$=total volume of mixture in milliliter
$V_g$=volume of gas as calculated using ideal gas law equation $$\text{Compressive Strength Calculation: CS} = 12.66\,(D)^{1.416} \quad \text{Eq. 5}$$

Where:
CS=compressive strength in psi
D=density in lb/cu.ft. (from foam density calculation)

$$\text{Tensile Strength Calculation: TS} = 23.01\,(D)^{1.1115} \quad \text{Eq. 6}$$

TS=tensile strength in psi
D=density in lb/cu.ft. (from foam density calculation)

$$\text{Flexural Strength Calculation: FS} = 18.99\,(D)^{1.3769} \quad \text{Eq. 7}$$

Where:
FS=tensile strength in psi
D=density in lb/cu.ft. (from foam density calculation)

Thus by running the calculations in order as described in Equations 1-7 above the formulator can estimate the foamed density 118, and the compressive 124, tensile 126, and flexural 128 strength of the formulated product. The Equations 1-7 can be calculated by hand or with the aid of a slide rule and mathematical tables or a hand held calculator. It is best, however, to employ some computing means, such as a computer comprising a microprocessor and basic input output system. The equations can be hardwired into the microprocessor or preferably accomplished by installed software.

Sample formulations are provided for below:

EXAMPLE 1

| RAW MATERIAL | Density (g/mL) | wt. (g) | Vol. (mL) |
|---|---|---|---|
| PART B | | | |
| Terate 4020 | 1.200 | 43.11 | 35.93 |
| Voranol 490 | 1.109 | 19.95 | 17.99 |
| Saytex RB7001 | 1.480 | 25.00 | 16.89 |
| Glycerine | 1.100 | 2.29 | 2.08 |
| 245fa | 1.320 | 6.00 | 4.55 |
| Pelron 9475 | 1.000 | 1.00 | 1.00 |
| Polycat 8 | 0.870 | 1.25 | 1.44 |
| WATER | 1.000 | 1.40 | 1.40 |
| TOTAL | | 100.00 | 81.27 |
| PART A | | | |
| PAPI 27 | 1.240 | 100.80 | 81.29 |

Index: 1.093
Volume ratio: 1.00
Experimental compressive strength parallel to rise (psi): 76.8
Calculated compressive strength (psi): 78.6

EXAMPLE 2

| RAW MATERIAL | Density (g/mL) | wt. (g) | Vol. (mL) |
|---|---|---|---|
| PART B | | | |
| Terate 4020 | 1.200 | 40.26 | 33.55 |
| Voranol 370 | 1.110 | 16.05 | 14.46 |
| Saytex RB-7001 | 1.480 | 20.00 | 13.51 |
| cyclopentane | 0.749 | 20.00 | 26.70 |
| Silbyk TP3811 | 1.040 | 1.61 | 1.55 |
| Dabco K-15 | 1.110 | 1.28 | 1.16 |
| Toyocat TR-20 | 1.010 | 0.80 | 0.79 |
| TOTAL | | 100.00 | 91.72 |
| PART A | | | |
| PAPI 27 | | 132.55 | 106.90 |

Index: 2.700
Volume ratio: 1.165
Experimental compressive strength parallel to rise (psi): 29.9
Calculated compressive strength (psi): 26.2

EXAMPLE 3

| RAW MATERIAL | Density (g/mL) | wt. (g) | Vol. (mL) |
|---|---|---|---|
| PART B | | | |
| Terate 4020 | 1.200 | 45.25 | 37.71 |
| Voranol 370 | 1.110 | 16.05 | 14.46 |
| Saytex RB-7980 | 1.650 | 15.01 | 9.10 |
| Cyclopentane | 0.749 | 20.00 | 26.70 |
| Silbyk TP3811 | 1.040 | 1.61 | 1.55 |
| Dabco K-15 | 1.110 | 1.28 | 1.16 |
| Toyocat TR-20 | 1.010 | 0.80 | 0.79 |
| TOTAL | | 100.00 | 91.46 |
| PART A | | | |
| PAPI 27 | 1.240 | 146.40 | 118.06 |

Index: 2.700
Volume ratio: 1.291
Experimental Free rise density (pcf): 1.84
Experimental compressive strength parallel to rise (psi): 31.7
Calculated compressive strength (psi): 30.0

EXAMPLE 4

| RAW MATERIAL | Density (g/mL) | wt. (g) | Vol. (mL) |
|---|---|---|---|
| PART B | | | |
| Poly G 30-240 | 1.029 | 75.48 | 73.35 |
| Poly G 76-635 | 1.091 | 17.05 | 15.63 |
| WATER | 1.000 | 2.22 | 2.22 |
| DC198 | 1.040 | 0.75 | 0.72 |
| DABCO 33LV | 1.130 | 4.50 | 3.98 |
| Dabco BL-11 | 0.900 | 1.00 | 1.11 |
| TOTAL | 1.041 | 101.00 | 97.02 |
| PART A | | | |
| Rubinate M | 1.240 | 120.30 | 97.02 |

Index: 1.106
Volume ratio: 1.000
User defined exotherm (C): 130
Pre-calculated free-rise density (pcf): 3.23
Experimental free rise density (pcf): 3.25

EXAMPLE 5

| RAW MATERIAL | Density (g/mL) | wt. (g) | Vol. (mL) |
|---|---|---|---|
| PART B | | | |
| Carpol GSP280 | 1.106 | 11.95 | 10.81 |
| Biosoft N91-8 | 1.008 | 15.00 | 14.88 |
| TCPP | 1.295 | 60.00 | 46.33 |
| DC198 | 1.040 | 3.00 | 2.88 |
| WATER | 1.000 | 5.87 | 5.87 |
| Toyocat DM-70 | 0.990 | 0.87 | 0.88 |
| Polycat SA-1 | 1.070 | 1.17 | 1.09 |
| Dabco TMR | 1.050 | 2.14 | 2.04 |
| TOTAL: | 1.179 | 100.00 | 84.79 |
| PART A | | | |
| Rubinate M | 1.240 | 210.30 | 169.60 |

Index: 2.045
Volume ratio: 1.000
User defined exotherm (C): 150
Pre-calculated free-rise density (pcf): 1.67
Experimental free rise density (pcf): 1.67

Examples 1-5 indicate that the invention is capable of predicting physical properties of a rigid polyurethane foams. Allowing the formulator estimate the physical properties prior to determining them experimentally saves time, materials and reduces waste. Having set forth the general nature and specific embodiment(s) of the invention, the true scope is now particularly pointed out in the appended claims.

What is claimed is:

1. A method of creating a recipe for a polyurethane foam comprising: (a) populating a database means with physical properties of at least two raw materials; (b) determining design criteria for a polyurethane foam; (c) selecting at least two raw materials from said database means; (d) selecting at least one blowing agent; (e) formulating by proportioning said raw materials and said blowing agent with respect to each other; (f) calculating the physical properties of said polyurethane foam by applying an algorithm means to said physical properties of said raw materials, said blowing agent and said proportions using a calculating means; wherein said calculating means further comprises a microprocessor, an input output system and software; (g) comparing said calculated physical properties to said design criteria; (h) reformulating by repeating steps (a) through (g) until said design criteria are met; (i) creating said recipe for said polyurethane foam by recording the proportions of said raw materials and said blowing agent in a tangible medium.

2. The method of claim 1 wherein said software is a spread sheet program capable of creating said database means, accepting proportional values of said formula, and performing mathematical operations on said proportions, said blowing agent, and said physical properties of said raw materials using said algorithm means.

3. The method of claim 1 wherein said calculating means is programmable logic controller capable of creating said database means, accepting said proportions of said raw materials and said blowing agent, performing mathematical operations on said values of said physical properties of said raw materials, said blowing agent, and said proportions using said algorithm means; and displaying said calculated physical properties and said proportions of said raw materials and said blowing agent.

4. The method of claim 1 wherein at least one of the raw materials is a polyol and at least one of the raw materials is an isocyanate.

5. The method of claim 1 wherein said design criteria of said polyurethane foam further comprises; (a) an index; (b) a volume ratio;
   (c) a compressive strength; (d) a free rise density and; (e) an exotherm not higher than 150C.

6. A method of creating a recipe for a polyurethane foam with:
   (i) an index of at least 1.000;
   (ii) a volume ratio of at least 1.00;
   (iii) a compressive strength of at least 30 psi;
   (iv) a free rise density of at least 1.0 pcf;
   comprising: (a) populating a database means with physical properties of at least two raw materials; (b) selecting at least two raw materials from said database means;
   (d) selecting at least one blowing agent; (e) formulating by proportioning said raw materials and said blowing agent with respect to each other; (f) calculating the physical properties of said polyurethane foam by applying an algorithm means to said physical properties of said raw materials, said blowing agent, and said proportions using a calculating means; wherein said calculating means further comprises a microprocessor, an input output system and software; (g) comparing said calculated physical properties to said design criteria; (h) reformulating by repeating steps (a) through (g) until said design criteria are met; (i) creating said recipe for said polyurethane foam by recording the proportions of said raw materials and said blowing agent in a tangible medium.

7. The method of claim 6 wherein said software is a spread sheet program capable of creating said database means, accepting proportional values of said formula, and performing mathematical operations on said proportions; and said physical properties of said raw materials, said blowing agent using said algorithm means.

8. The method of claim 6 wherein said calculating means is programmable logic controller capable of creating said database means, accepting of said raw materials and said blowing agent, performing mathematical operations on said values of said physical properties of said raw materials, said blowing agent, and said proportions using said algorithm means; and
   displaying said calculated physical properties and said proportions of said raw materials and said blowing agent.

9. The method of claim 6 wherein at least one of the raw materials is a polyol and at least one of the raw materials is an isocyanate.

* * * * *